US012635927B2

(12) United States Patent
Wu et al.

(10) Patent No.: US 12,635,927 B2
(45) Date of Patent: May 26, 2026

(54) SINGLE-ARM ECG SIGNAL MEASUREMENT DEVICE AND SINGLE-ARM ECG SIGNAL MEASUREMENT METHOD

(71) Applicant: Chung Yuan Christian University, Taoyuan City (TW)

(72) Inventors: Shi-Yi Wu, Taoyuan City (TW); Shao-Hung Lu, Taoyuan City (TW); En Chuang, Taoyuan City (TW); Mei-Fen Chen, Taoyuan City (TW); Wen-Chi Lin, Taoyuan City (TW); Cheng Lun Tsai, Taoyuan City (TW); Kang-Ping Lin, Taoyuan City (TW)

(73) Assignee: Chung Yuan Christian University, Taoyuan City (TW)

( * ) Notice: Subject to any disclaimer, the term of this patent is extended or adjusted under 35 U.S.C. 154(b) by 180 days.

(21) Appl. No.: 18/797,527

(22) Filed: Aug. 8, 2024

(65) Prior Publication Data
US 2025/0344982 A1 Nov. 13, 2025

(30) Foreign Application Priority Data

May 8, 2024 (TW) ................................ 113117067

(51) Int. Cl.
*A61B 5/327* (2021.01)
*A61B 5/00* (2006.01)

(52) U.S. Cl.
CPC ............ *A61B 5/327* (2021.01); *A61B 5/6824* (2013.01); *A61B 2562/043* (2013.01)

(58) Field of Classification Search
CPC . A61B 5/327; A61B 5/6824; A61B 2562/043; A61B 5/332; A61B 5/282
See application file for complete search history.

(56) References Cited

U.S. PATENT DOCUMENTS

2007/0293781 A1* 12/2007 Sims ........................ A61B 5/72
600/534
2010/0168530 A1* 7/2010 Chetham .............. A61B 5/6843
600/301
2021/0345932 A1* 11/2021 Nguyen ............... A61B 5/0002

FOREIGN PATENT DOCUMENTS

CN        104902812      9/2015
WO       2013075270      5/2013
WO       2013075388      5/2013

OTHER PUBLICATIONS

"Office Action of Taiwan Counterpart Application", issued on Sep. 4, 2024, p. 1-p. 9.

* cited by examiner

*Primary Examiner* — Joel Lamprecht
(74) *Attorney, Agent, or Firm* — JCIPRNET

(57) ABSTRACT

Disclosed are a single-arm electrocardiogram (ECG) signal measurement device and a single-arm ECG signal measurement method. The single-arm ECG signal measurement device includes a first sensing electrode, a second sensing electrode, a third sensing electrode, a fourth sensing electrode, a fifth sensing electrode, a sixth sensing electrode, and a computing circuit. The first sensing electrode, the second sensing electrode, the third sensing electrode, the fourth sensing electrode, the fifth sensing electrode, and the sixth sensing electrode receive physiological signals from six different positioning points located on an upper arm of a user. The computing circuit generates ECG signals according to the physiological signals, and generates a 12-lead ECG-like signal according to the ECG signals.

20 Claims, 6 Drawing Sheets

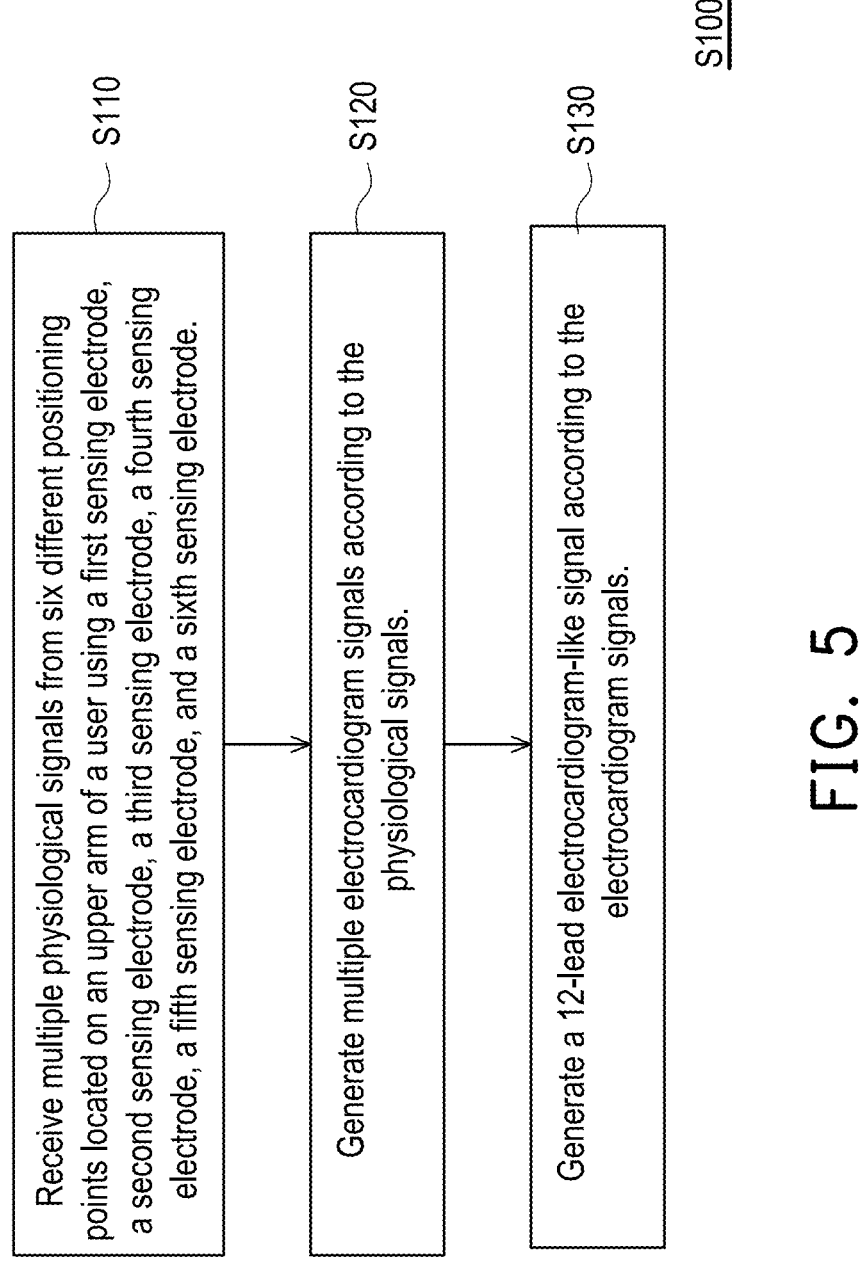

S100

S110 — Receive multiple physiological signals from six different positioning points located on an upper arm of a user using a first sensing electrode, a second sensing electrode, a third sensing electrode, a fourth sensing electrode, a fifth sensing electrode, and a sixth sensing electrode.

S120 — Generate multiple electrocardiogram signals according to the physiological signals.

S130 — Generate a 12-lead electrocardiogram-like signal according to the electrocardiogram signals.

FIG. 5

SINGLE-ARM ECG SIGNAL MEASUREMENT DEVICE AND SINGLE-ARM ECG SIGNAL MEASUREMENT METHOD

CROSS-REFERENCE TO RELATED APPLICATION

This application claims the priority benefit of Taiwan application serial no. 113117067, filed on May 8, 2024. The entirety of the above-mentioned patent application is hereby incorporated by reference herein and made a part of this specification.

BACKGROUND

Technical Field

The disclosure relates to a physiological signal measurement device and a physiological signal measurement method, and in particular to a single-arm electrocardiogram (ECG) signal measurement device and a single-arm ECG signal measurement method.

Description of Related Art

Current physiological signal measurement instruments require ten sensing electrodes to measure a user, thereby generating 12-lead electrocardiogram (ECG) signals. Six of the ten sensing electrodes are disposed on the user's chest. The remaining four sensing electrodes are respectively disposed on the user's limbs. This operation needs to be performed by professional medical personnel, which makes long-term monitoring impractical. Moreover, the large number of sensing electrodes and wires may cause discomfort for the user during testing. The application of ECGs obtained through the 12-leads is crucial clinically, especially for heart disease diagnosis. Thus, how to measure 12-lead ECGs in a more convenient manner and develop applications in long-term monitoring is one of the focuses of research for those skilled in the art.

SUMMARY

The disclosure provides a single-arm electrocardiogram signal measurement device and a single-arm electrocardiogram signal measurement method, realizing electrocardiogram signal measurement on an arm and reducing the number of electrodes used. By deducing signals sensed from different electrodes, an electrocardiogram signal similar to a 12-lead electrocardiogram signal is obtained.

In an embodiment of the disclosure, the single-arm electrocardiogram signal measurement device includes a first sensing electrode, a second sensing electrode, a third sensing electrode, a fourth sensing electrode, a fifth sensing electrode, a sixth sensing electrode, and a computing circuit. The first sensing electrode, the second sensing electrode, the third sensing electrode, the fourth sensing electrode, the fifth sensing electrode, and the sixth sensing electrode receive multiple physiological signals from six different positioning points located on an upper arm of a user. The computing circuit is coupled to the first sensing electrode, the second sensing electrode, the third sensing electrode, the fourth sensing electrode, the fifth sensing electrode, and the sixth sensing electrode. The computing circuit generates multiple electrocardiogram signals according to the physiological signals, and generates a 12-lead electrocardiogram-like signal according to the electrocardiogram signals.

In an embodiment of the disclosure, a single-arm electrocardiogram signal measurement method includes the following steps. Multiple physiological signals are received from six different positioning points located on an upper arm of a user using a first sensing electrode, a second sensing electrode, a third sensing electrode, a fourth sensing electrode, a fifth sensing electrode, and a sixth sensing electrode. Multiple electrocardiogram signals are generated according to the physiological signals. A 12-lead electrocardiogram-like signal is generated according to the electrocardiogram signals.

Based on the above, the disclosure only needs six sensing electrodes to receive the six physiological signals located on the upper arm of the user and generate the 12-lead electrocardiogram-like signal according to the six physiological signals. It is noted that, compared to current measurement methods, a number of sensing electrodes needed is reduced in the disclosure. Thus, in the disclosure, the discomfort experienced by the user during the measurement can be reduced.

BRIEF DESCRIPTION OF THE DRAWINGS

FIG. 5 is a flowchart showing a single-arm ECG signal measurement method according to an embodiment of the disclosure.

DESCRIPTION OF THE EMBODIMENTS

Figure 1:
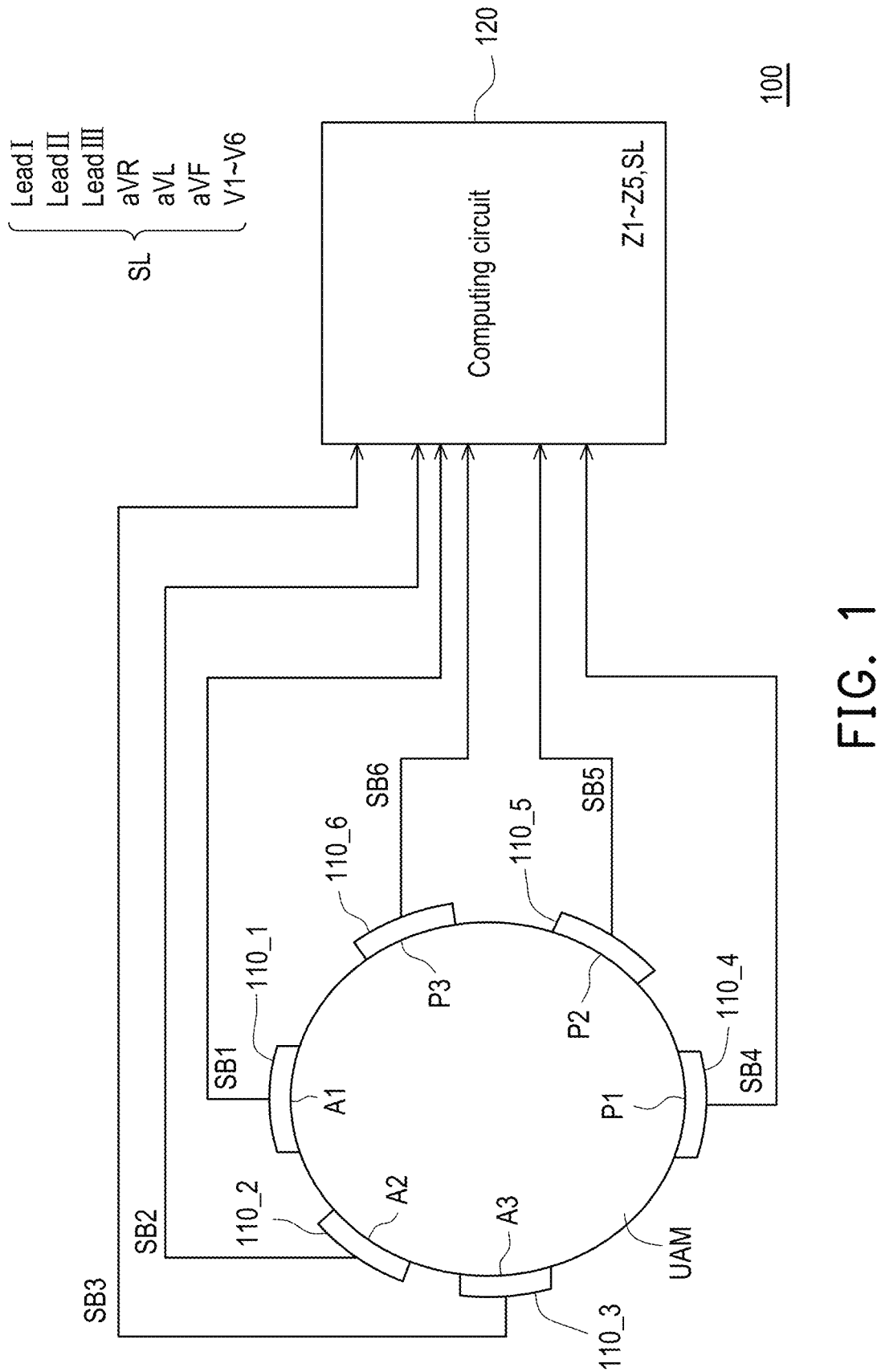
FIG. 1 is a schematic diagram showing a single-arm electrocardiogram (ECG) signal measurement device according to an embodiment of the disclosure.

Some of the exemplary embodiments of the disclosure will be described in detail with the accompanying drawings. The reference numerals used in the following description will be regarded as the same or similar components when the same reference numerals appear in different drawings. These exemplary embodiments are only a part of the disclosure, and do not disclose all of the ways in which this disclosure can be implemented. More specifically, these exemplary embodiments are only examples of the device and method in the claims of the disclosure.

Please refer to FIG. 1. FIG. 1 is a schematic diagram of a single-arm electrocardiogram (ECG) signal measurement device according to an embodiment of the disclosure. In this embodiment, a single-arm ECG signal measurement device 100 includes multiple sensing electrodes 110_1 to 110_6 and a computing circuit 120. The sensing electrodes 110_1 to 110_6 receive multiple physiological signals SB1 to SB6 from six different positioning points A1 to A3 and P1 to P3 located on an upper arm UAM of a user.

In this embodiment, the upper arm UAM may be a left upper arm. The sensing electrodes 110_1 to 110_6 receive the physiological signals SB1 to SB6 from the positioning points A1 to A3 and P1 to P3 located on the left upper arm of the user. For example, the sensing electrode 110_1 receives the physiological signal SB1 from the positioning point A1 located on the upper arm UAM. The sensing electrode 110_2 receives the physiological signal SB2 from the positioning point A2 located on the upper arm UAM. The sensing electrode 110_3 receives the physiological signal SB3 from the positioning point A3 located on the upper arm UAM. The sensing electrode 110_4 receives the physiological signal SB4 from the positioning point P1 located on the upper arm UAM. The sensing electrode 110_5 receives the physiological signal SB5 from the positioning point P2 located on the upper arm UAM. The sensing electrode 110_6 receives the physiological signal SB6 from the positioning point P3 located on the upper arm UAM.

In this embodiment, the computing circuit 120 is coupled to the sensing electrodes 110_1 to 110_6. The computing circuit 120 generates multiple ECG signals Z1 to Z5 according to the physiological signals SB1 to SB6. The computing circuit 120 generates a 12-lead ECG-like signal SL according to the ECG signals Z1 to Z5.

It is worth mentioning that the single-arm ECG signal measurement device 100 only needs six sensing electrodes 110_1 to 110_6 to receive six physiological signals SB1 to SB6 from the upper arm UAM of the user and generate the 12-lead ECG-like signal SL according to the six physiological signals SB1 to SB6. Compared to current measurement methods, the number of the sensing electrodes 110_1 to 110_6 that the single-arm ECG signal measurement device 100 needs can be reduced. This way, the single-arm ECG signal measurement device 100 can reduce the discomfort experienced by the user during the measurement. In addition, the single-arm ECG signal measurement device 100 only receives the physiological signals SB1 to SB6 from the positioning points A1 to A3 and P1 to P3 located on the upper arm UAM. Thus, compared to current measurement methods, the single-arm ECG signal measurement device 100 is more convenient for use.

In this embodiment, the computing circuit 120 may be, for example, a central processing unit (CPU) or other programmable general-purpose or special-purpose microprocessors, digital signal processors (DSP), programmable controllers, application specific integrated circuits (ASIC), programmable logic devices (PLD), or other similar devices or combinations thereof capable of loading and executing computer programs.

Figure 2:
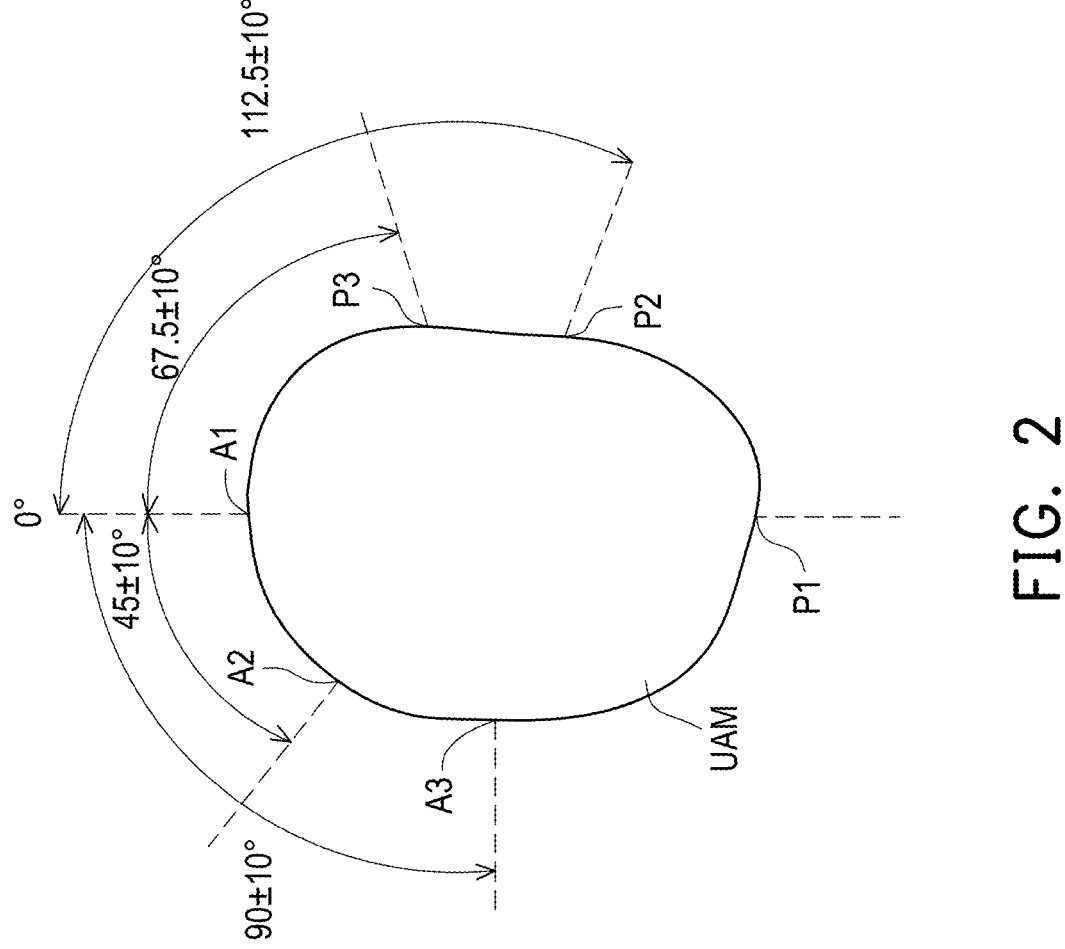
FIG. 2 is a schematic diagram showing positioning points according to an embodiment of the disclosure.

Please refer to FIGS. 1 and 2. FIG. 2 is a schematic diagram showing positioning points according to an embodiment of the disclosure. In this embodiment, the sensing electrode 110_1 receives the physiological signal SB1 from the positioning point A1 located on the upper arm UAM. For example, the sensing electrode 110_1 is attached to the positioning point A1 located on a front end of the biceps of the upper arm UAM to receive the physiological signal SB1.

The sensing electrode 110_2 receives the physiological signal SB2 from the positioning point A2 shifted approximately 45±10° (i.e., 35° to 55°) towards an outside of the upper arm UAM from the front end (i.e., the positioning point A1). For example, with a cross-section of the upper arm UAM as the center of circle, there is an angular offset of approximately −45±10° (which is not a limitation of the disclosure) between the positioning point A2 and the positioning point A1. The sensing electrode 110_2 is attached to the positioning point A2 to receive the physiological signal SB2.

The sensing electrode 110_3 receives the physiological signal SB3 from the positioning point A3 shifted approximately 90±10° (i.e., 80° to 100°) towards the outside of the upper arm UAM from the front end (i.e., the positioning point A1). For example, with the cross-section of the upper arm UAM as the center of circle, there is an angular offset of approximately −90±10° (which is not a limitation of the disclosure) between the positioning point A3 and the positioning point A1. The sensing electrode 110_3 is attached to the positioning point A3 to receive the physiological signal SB3.

The sensing electrode 110_4 receives the physiological signal SB4 from the positioning point P1 located on a rear end of the upper arm UAM. For example, the sensing electrode 110_4 is attached to the positioning point P1 on the triceps of the upper arm UAM to receive the physiological signal SB4. With the cross-section of the upper arm UAM as the center of circle, there is an angular offset of approximately 180±10° (i.e., 190° to 170°, which is not a limitation of the disclosure) between the positioning point P1 and the positioning point A1.

The sensing electrode 110_5 receives the physiological signal SB5 from the positioning point P2 shifted approximately 67.5±10° (i.e., 57.5° to) 77.5° towards an inside of the upper arm UAM from the front end (i.e., the positioning point A1). For example, the sensing electrode 110_5 is attached to the positioning point P2 on the upper arm UAM to receive the physiological signal SB5. With the cross-section of the upper arm UAM as the center of circle, there is an angular offset of approximately +67.5±10° (which is not a limitation of the disclosure) between the positioning point P2 and the positioning point A1.

The sensing electrode 110_6 receives the physiological signal SB6 from the positioning point P3 shifted approximately 112.5±10° (i.e., 102.5° to) 122.5° towards the inside of the upper arm UAM from the front end (i.e., the positioning point A1). For example, the sensing electrode 110_6 is attached to the positioning point P3 on the upper arm UAM to receive the physiological signal SB6. With the cross-section of the upper arm UAM as the center of circle, there is an angular offset of approximately +112.5±10° (which is not a limitation of the disclosure) between the positioning point P3 and the positioning point A1.

In this embodiment, the computing circuit 120 receives the physiological signals SB1 to SB6. The computing circuit 120 generates the ECG signal Z1 according to a potential difference between the physiological signals SB2 and SB6 (e.g., Z1=SB2−SB6). For example, the computing circuit 120 uses the sensing electrodes 110_2 and 110_6 as a sensing electrode pair to generate the ECG signal Z1. The computing circuit 120 generates the ECG signal Z2 according to a potential difference between the physiological signals SB1 and SB4 (e.g., Z2=SB1−SB4). For example, the computing circuit 120 uses the sensing electrodes 110_1 and 110_4 as a sensing electrode pair to generate the ECG signal Z2. The computing circuit 120 generates the ECG signal Z3 according to a potential difference between the physiological signals SB3 and SB1 (e.g., Z3=SB3−SB1). For example, the computing circuit 120 uses the sensing electrodes 110_3 and 110_1 as a sensing electrode pair to generate the ECG signal Z3. The computing circuit 120 generates the ECG signal Z4 according to a potential difference between the physiological signals SB3 and SB5 (e.g., Z4=SB3−SB5). For example, the computing circuit 120 uses the sensing electrodes 110_3 and 110_5 as a sensing electrode pair to generate the ECG signal Z4. The computing circuit 120 generates the ECG signal Z5 according to a potential difference between the physiological signals SB3 and SB6 (e.g., Z5=SB3−SB6). For example, the computing circuit 120 uses the sensing electrodes 110_3 and 110_6 as a sensing electrode pair to generate the ECG signal Z5. Thus, the computing circuit 120 can generate the ECG signals Z1 to Z5 in different time periods.

In some embodiments, the computing circuit 120 may generate the ECG signals Z1 to Z5 simultaneously after receiving the physiological signals SB1 to SB6.

The computing circuit 120 generates multiple lead signals of the 12-lead ECG-like signal SL at least according to the ECG signals Z1 to Z5.

In this embodiment, the computing circuit 120 generates multiple bipolar limb lead signals Lead I, Lead II, and Lead III as well as multiple augmented unipolar limb lead signals aVR, aVL, and aVF of the 12-lead ECG-like signal SL according to the ECG signals Z1 and Z2.

The computing circuit 120 multiplies the ECG signal Z1 by a first constant C0 to generate the bipolar limb lead signal Lead I of the 12-lead ECG-like signal SL (e.g., Lead I=C0×Z1). The computing circuit 120 multiplies the ECG signal Z2 by the first constant C0 to generate the bipolar limb lead signal Lead II of the 12-lead ECG-like signal SL (e.g., Lead II=C×Z2). In addition, the computing circuit 120 subtracts the ECG signal Z1 from the ECG signal Z2 to generate the bipolar limb lead signal Lead III of the 12-lead ECG-like signal SL (e.g., Lead III=Z2–Z1). In this embodiment, the first constant C0 falls between 0.5 and 1.5.

In this embodiment, the computing circuit 120 may generate the augmented unipolar limb lead signal aVR of the 12-lead ECG-like signal SL according to Formula (1). The augmented unipolar limb lead signal aVR may be referred to as an augmented unipolar right upper limb lead signal.

$$aVR = -\left(\frac{Z1}{2}\right) - \left(\frac{Z2}{2}\right) \qquad \text{Formula (1)}$$

In other words, the computing circuit 120 divides the ECG signal Z1 by 2 to generate a first partial pressure signal, divides the ECG signal Z2 by 2 to generate a second partial pressure signal, and subtracts the second partial pressure signal from an inverted signal of the first partial pressure signal to generate the augmented unipolar limb lead signal aVR.

The computing circuit 120 may generate the augmented unipolar limb lead signal aVL of the 12-lead ECG-like signal SL according to Formula (2). The augmented unipolar limb lead signal aVL may be referred to as an augmented unipolar left upper limb lead signal.

$$aVL = \left(\frac{Z1}{2}\right) - \left(\frac{Z2 - Z1}{2}\right) \qquad \text{Formula (2)}$$

In other words, the computing circuit 120 subtracts the ECG signal Z1 from the ECG signal Z2 to generate a differential signal, and divides the differential signal by 2 to generate a third partial pressure signal. The computing circuit 120 subtracts the third partial pressure signal from the first partial pressure signal to generate the augmented unipolar limb lead signal aVL.

The computing circuit 120 may generate the augmented unipolar limb lead signal aVF of the 12-lead ECG-like signal SL according to Formula (3). The augmented unipolar limb lead signal aVF may be referred to as an augmented unipolar left lower limb lead signal.

$$aVF = \left(\frac{Z1}{2}\right) + \left(\frac{Z2 - Z1}{2}\right) \qquad \text{Formula (3)}$$

In other words, the computing circuit 120 adds the third partial pressure signal to the first partial pressure signal to generate the augmented unipolar limb lead signal aVF.

In this embodiment, the computing circuit 120 generates multiple chest lead signals V1 to V6 of the 12-lead ECG-like signal SL according to the ECG signals Z2 to Z5.

The computing circuit 120 multiplies the ECG signal Z3 by the first constant C0 to generate the chest lead signal V1 of the 12-lead ECG-like signal SL (e.g., V1=C0×Z3). The computing circuit 120 adds the ECG signal Z5 to the ECG signal Z4 (e.g., Z4+Z5) to generate a sum signal, and uses the sum signal as the chest lead signal V2 of the 12-lead ECG-like signal SL (e.g., V2=Z4+Z5).

The computing circuit 120 may generate the chest lead signal V3 of the 12-lead ECG-like signal SL according to Formula (4).

$$V3 = C1 \times Z2 + C2 \times (Z4 + Z5) \qquad \text{Formula (4)}$$

"C1" is a second constant. "C2" is a third constant. In other words, the computing circuit 120 multiplies the ECG signal Z2 by the second constant C1 to generate a first product signal, and multiplies the sum signal by the third constant C2 to generate a second product signal. The computing circuit 120 adds the second product signal to the first product signal to generate the chest lead signal V3. In this embodiment, the second constant C1 and the third constant C2 may be adjusted. For example, the second constant C1 falls between 0.2 and 0.4. The third constant C2 falls between 0.5 and 0.7.

The computing circuit 120 may generate the chest lead signal V4 of the 12-lead ECG-like signal SL according to Formula (5).

$$V4 = C1 \times Z2 + C2 \times Z3 \qquad \text{Formula (5)}$$

In other words, the computing circuit 120 multiplies the ECG signal Z3 by the third constant C2 to generate a third product signal, and adds the third product signal to the first product signal to generate the chest lead signal V4.

The computing circuit 120 may generate the chest lead signal V5 of the 12-lead ECG-like signal SL according to Formula (6).

$$V5 = C2 \times Z2 + C1 \times (Z4 + Z5) \qquad \text{Formula (6)}$$

In other words, the computing circuit 120 multiplies the ECG signal Z2 by the third constant C2 to generate a fourth product signal, and multiplies the sum signal (e.g., Z4+Z5) by the second constant C1 to generate a fifth product signal. The computing circuit 120 adds the fifth product signal to the fourth product signal to generate the chest lead signal V5.

The computing circuit 120 may generate the chest lead signal V6 of the 12-lead ECG-like signal SL according to Formula (7).

$$V6 = C2 \times Z2 + C1 \times Z3 \qquad \text{Formula (7)}$$

In other words, the computing circuit 120 multiplies the ECG signal Z3 by the second constant C1 to generate a sixth product signal, and adds the sixth product signal to the fourth product signal to generate the chest lead signal V6.

In this embodiment, the 12-lead ECG-like signal SL may be referred to as the "simulated 12-lead ECG signal SL".

In this embodiment, based on the actual usage or design, the positioning points A1 to A3 and P1 to P3 may be slightly adjusted, switched, or changed. Thus, a computing method of the 12-lead ECG-like signal SL may be slightly adjusted, switched, or changed correspondingly. In addition, the first constant C0, the second constant C1, and the third constant C2 may be adjusted to make the results of the 12-lead ECG-like signal SL closer to the results of an actual 12-lead ECG signal.

Figure 3:
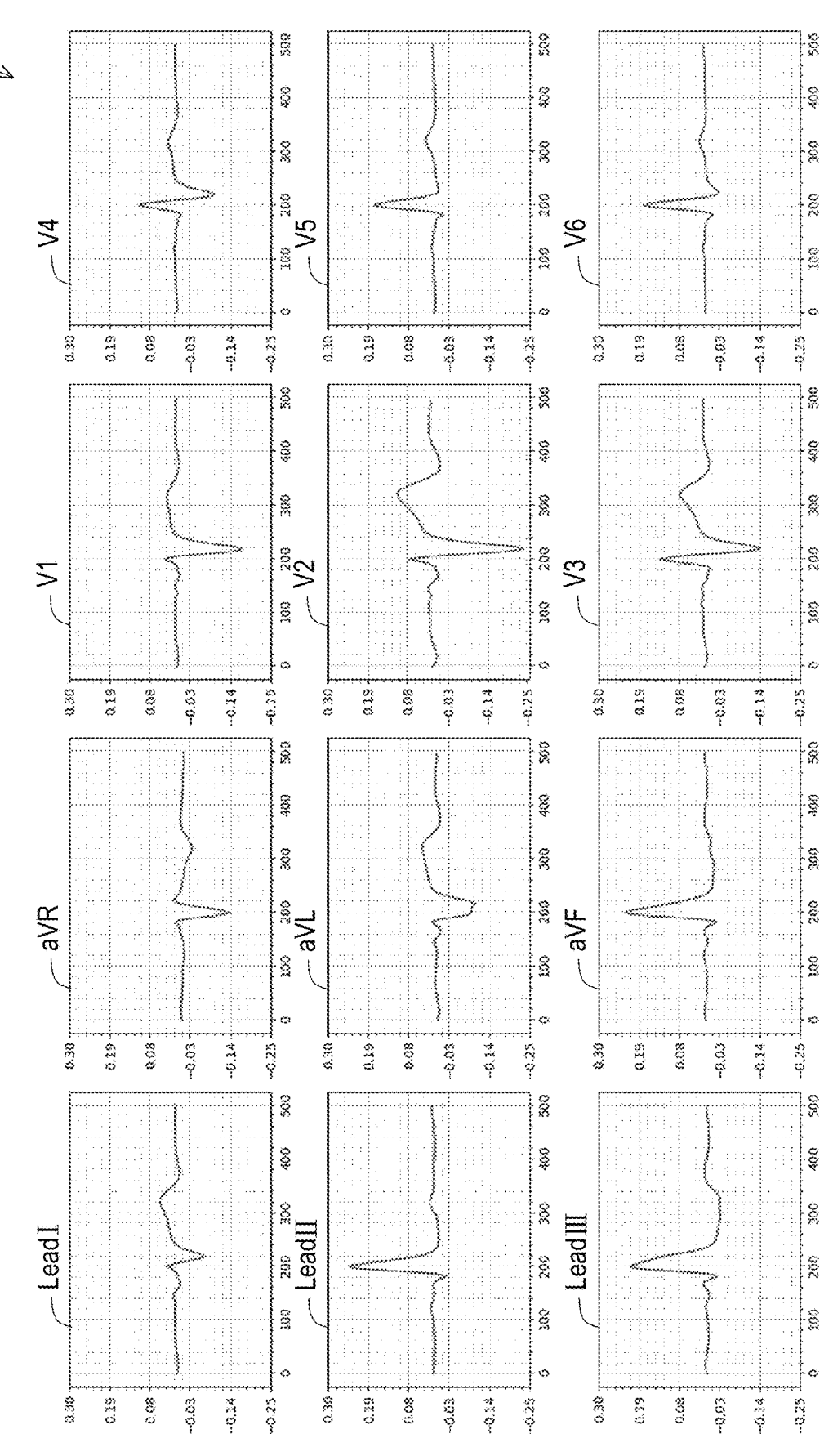
FIG. 3 is a waveform diagram of a 12-lead ECG-like signal generated according to an embodiment of the disclosure.
Figure 4:
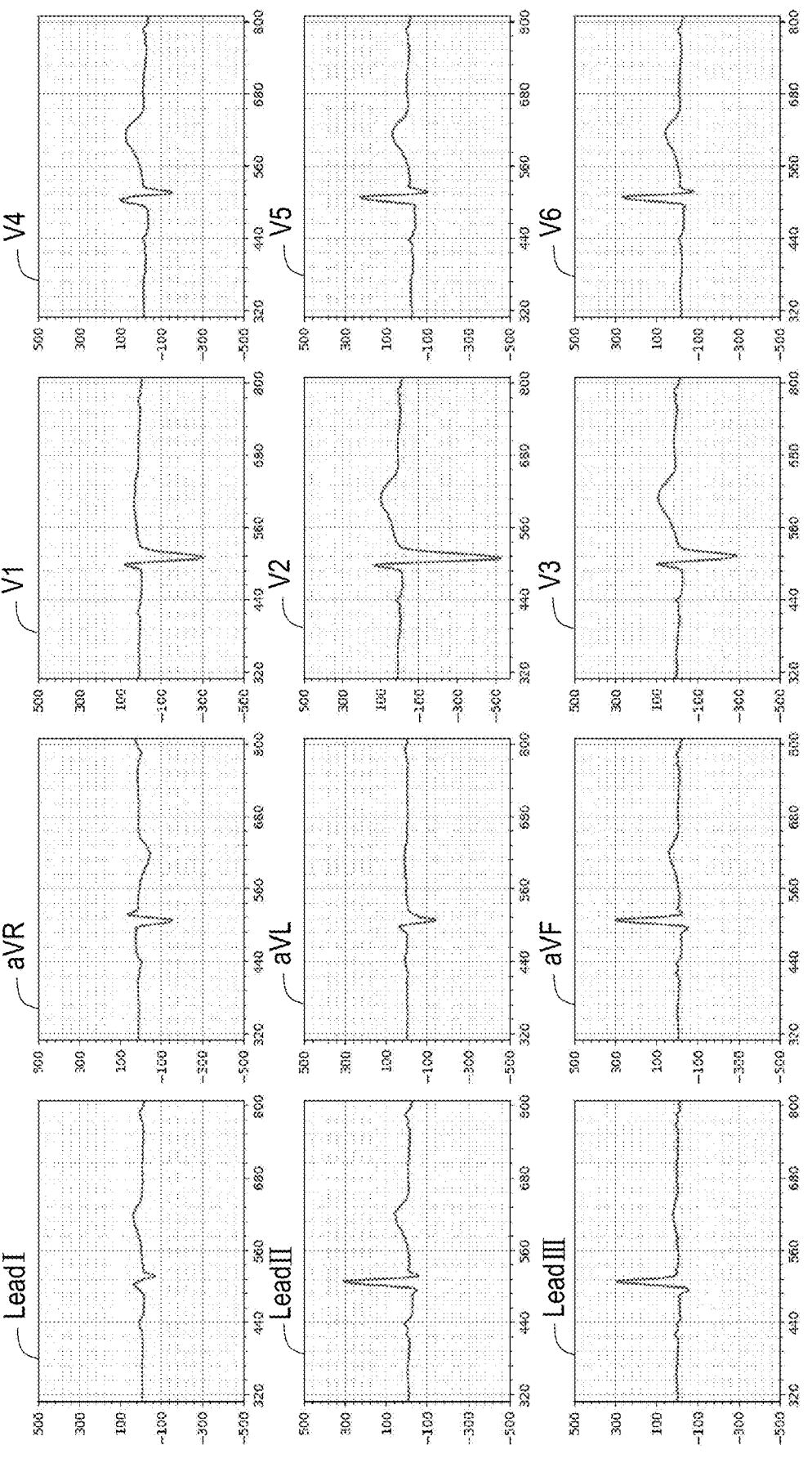
FIG. 4 is a waveform diagram of a 12-lead ECG-like signal generated by a current measurement instrument.

Please refer to FIGS. 1, 3, and 4. FIG. 3 is a waveform diagram of a 12-lead ECG-like signal generated according to an embodiment of the disclosure. FIG. 4 is a waveform diagram of a 12-lead ECG-like signal generated by a current measurement instrument. In this embodiment, FIG. 3 shows the waveform diagram of the 12-lead ECG-like signal SL of the single-arm ECG signal measurement device 100. The 12-lead ECG-like signal SL includes the bipolar limb lead signals Lead I, Lead II, and Lead III. The 12-lead ECG-like signal SL also includes the augmented unipolar limb lead signals aVR, aVL, and aVF as well as the chest lead signals V1 to V6.

It is noted that the waveforms of all wavebands of the bipolar limb lead signals Lead I, Lead II, and Lead III, the augmented unipolar limb lead signals aVR, aVL, and aVF, and the chest lead signals V1 to V6 generated by the single-arm ECG signal measurement device 100 conform with the waveforms of all wavebands of the current measurement instruments. In other words, the bipolar limb lead signals Lead I, Lead II, and Lead III, the augmented unipolar limb lead signals aVR, aVL, and aVF, and the chest lead signals V1 to V6 generated by the single-arm ECG signal measurement device 100 show all wavebands (including the P wave, QRS complex, T wave, and U wave) in a normal cardiac cycle. Thus, the single-arm ECG signal measurement device 100 can replace current 12-lead ECG measurement instruments. The measurement may be performed on the user with the single-arm ECG signal measurement device 100 in areas outside of clinics and hospitals.

Please refer to FIGS. 1 and 5. FIG. 5 is a flowchart showing a single-arm ECG signal measurement method according to an embodiment of the disclosure. In this embodiment, a single-arm ECG signal measurement method S100 is applicable to the single-arm ECG signal measurement device 100. The single-arm ECG signal measurement method S100 includes Steps S110 to S130. In Step S110, the sensing electrodes 110_1 to 110_6 receive the physiological signals SB1 to SB6 from the different positioning points A1 to A3 and P1 to P3 located on the upper arm UAM of the user. In Step S120, the computing circuit 120 generates the ECG signals Z1 to Z5 according to the physiological signals SB1 to SB6. In Step S130, the computing circuit 120 generates the 12-lead ECG-like signal SL according to the ECG signals Z1 to Z5. The implementation examples of Steps S110 to S130 have been clearly described in the embodiments of FIGS. 1 and 2 and will not be repeated here.

Figure 6:
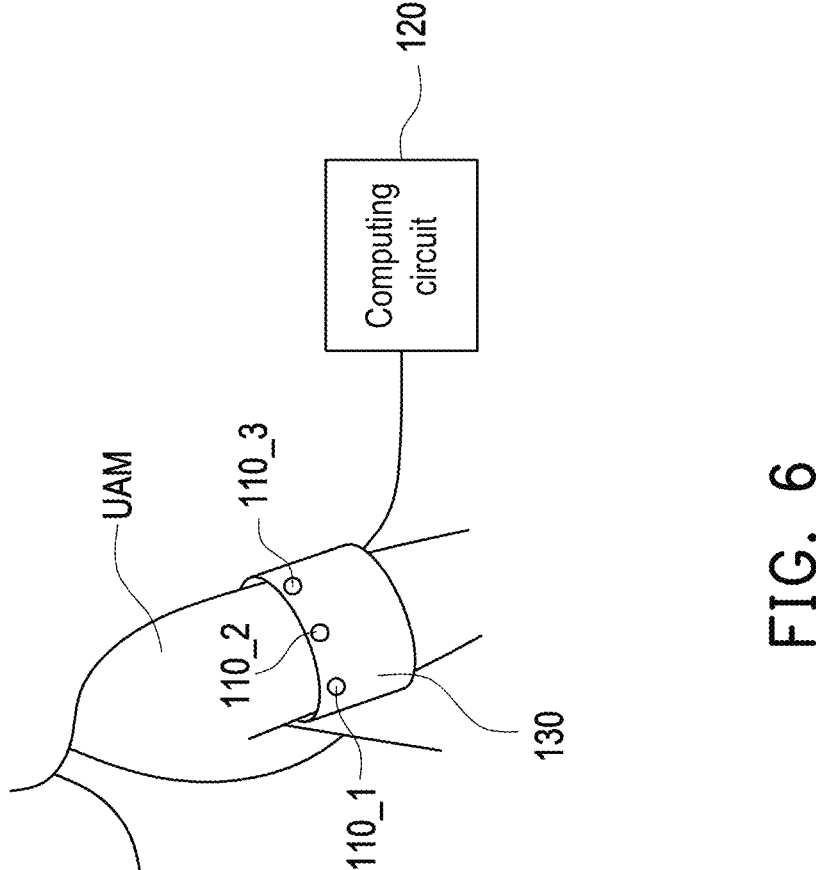
FIG. 6 is a measurement schematic diagram according to an embodiment of the disclosure.

Please refer to FIGS. 1 and 6. FIG. 6 is a measurement schematic diagram according to an embodiment of the disclosure. In this embodiment, the single-arm ECG signal measurement device 100 further includes a fixing unit 130. The sensing electrodes 110_1 to 110_6 are disposed on the fixing unit 130. During the measurement, the sensing electrodes 110_1 to 110_6 are fixed to the positioning points A1 to A3 and P1 to P3 on the upper arm UAM through the fixing unit 130. For example, during the measurement, the user puts on the fixing unit 130 and aligns a reference point of the fixing unit 130 with one of the positioning points A1 to A3 and P1 to P3. Thus, once the fixing unit 130 is put on, the sensing electrodes 110_1 to 110_6 are fixed to the positioning points A1 to A3 and P1 to P3 on the upper arm UAM.

In this embodiment, the fixing unit 130 may be implemented as an elastic arm strap or an inflatable arm strap with a fixing function (but the disclosure is not limited thereto).

In this embodiment, the computing circuit 120 may be disposed outside of the fixing unit 130. In some embodiments, the computing circuit 120 may be disposed on the fixing unit 130.

In summary, the single-arm ECG signal measurement device of the disclosure only needs six sensing electrodes to receive the six physiological signals located on the upper arm of the user and generate the 12-lead ECG-like signal according to the six physiological signals. Compared to current measurement methods, the number of sensing electrodes needed is reduced in the disclosure. This way, the single-arm ECG signal measurement device can reduce the discomfort experienced by the user during the measurement. In addition, compared to current measurement methods, the single-arm ECG signal measurement device is more convenient for use. Measurements may be performed on users with the single-arm ECG signal measurement devices in areas outside of clinics and hospitals.

Although the disclosure has been described with reference to the above embodiments, they are not intended to limit the disclosure. It will be apparent to one of ordinary skill in the art that modifications to the described embodiments may be made without departing from the spirit and the scope of the disclosure. Accordingly, the scope of the disclosure will be defined by the attached claims and their equivalents and not by the above detailed descriptions.

What is claimed is:

1. A single-arm electrocardiogram signal measurement device, comprising:
   a first sensing electrode, a second sensing electrode, a third sensing electrode, a fourth sensing electrode, a fifth sensing electrode, and a sixth sensing electrode, configured to receive a plurality of physiological signals from six different positioning points located on an upper arm of a user; and
   a computing circuit, coupled to the first sensing electrode, the second sensing electrode, the third sensing electrode, the fourth sensing electrode, the fifth sensing electrode, and the sixth sensing electrode, the computing circuit being configured to generate a plurality of electrocardiogram signals according to the plurality of physiological signals and generating a 12-lead electrocardiogram-like signal according to the plurality of electrocardiogram signals.

2. The single-arm electrocardiogram signal measurement device according to claim 1, wherein:
   the first sensing electrode receives a first physiological signal from a positioning point located at a front end of the upper arm,
   the second sensing electrode receives a second physiological signal from a positioning point shifted 45±10° towards an outside of the upper arm from the front end,
   the third sensing electrode receives a third physiological signal from a positioning point shifted 90±10° towards the outside of the upper arm from the front end, the fourth sensing electrode receives a fourth physiological signal from a positioning point located at a rear end of the upper arm, the fifth sensing electrode receives a fifth physiological signal from a positioning point shifted $67.5\pm10°$ towards an inside of the upper arm from the front end, and the sixth sensing electrode receives a sixth physiological signal from a positioning point shifted $112.5\pm10°$ towards the inside of the upper arm from the front end.

3. The single-arm electrocardiogram signal measurement device according to claim 2, wherein:

the computing circuit generates a first electrocardiogram signal according to a potential difference between the second physiological signal and the sixth physiological signal, the computing circuit generates a second electrocardiogram signal according to a potential difference between the first physiological signal and the fourth physiological signal, the computing circuit generates a third electrocardiogram signal according to a potential difference between the third physiological signal and the first physiological signal, the computing circuit generates a fourth electrocardiogram signal according to a potential difference between the third physiological signal and the fifth physiological signal, and the computing circuit generates a fifth electrocardiogram signal according to a potential difference between the third physiological signal and the sixth physiological signal.

4. The single-arm electrocardiogram signal measurement device according to claim 3, wherein:

the computing circuit multiplies the first electrocardiogram signal by a first constant to generate a first bipolar limb lead signal of the 12-lead electrocardiogram-like signal, and the computing circuit multiplies the second electrocardiogram signal by the first constant to generate a second bipolar limb lead signal of the 12-lead electrocardiogram-like signal.

5. The single-arm electrocardiogram signal measurement device according to claim 4, wherein the computing circuit subtracts the first electrocardiogram signal from the second electrocardiogram signal to generate a third bipolar limb lead signal of the 12-lead electrocardiogram-like signal.

6. The single-arm electrocardiogram signal measurement device according to claim 3, wherein the computing circuit divides the first electrocardiogram signal by 2 to generate a first partial pressure signal, divides the second electrocardiogram signal by 2 to generate a second partial pressure signal, and subtracts the second partial pressure signal from an inverted signal of the first partial pressure signal to generate a first augmented unipolar limb lead signal of the 12-lead electrocardiogram-like signal.

7. The single-arm electrocardiogram signal measurement device according to claim 6, wherein:

the computing circuit subtracts the first electrocardiogram signal from the second electrocardiogram signal to generate a differential signal, divides the differential signal by 2 to generate a third partial pressure signal, and subtracts the third partial pressure signal from the first partial pressure signal to generate a second augmented unipolar limb lead signal of the 12-lead electrocardiogram-like signal.

8. The single-arm electrocardiogram signal measurement device according to claim 7, wherein the computing circuit adds the third partial pressure signal to the first partial pressure signal to generate a third augmented unipolar limb lead signal of the 12-lead electrocardiogram-like signal.

9. The single-arm electrocardiogram signal measurement device according to claim 3, wherein:

the computing circuit multiplies the third electrocardiogram signal by a first constant to generate a first chest lead signal of the 12-lead electrocardiogram-like signal, and the computing circuit adds the fifth electrocardiogram signal to the fourth electrocardiogram signal to generate a sum signal, and uses the sum signal as a second chest lead signal of the 12-lead electrocardiogram-like signal.

10. The single-arm electrocardiogram signal measurement device according to claim 9, wherein:

the computing circuit multiplies the second electrocardiogram signal by a second constant to generate a first product signal, multiplies the sum signal by a third constant to generate a second product signal, and adds the second product signal to the first product signal to generate a third chest lead signal of the 12-lead electrocardiogram-like signal, the computing circuit multiplies the third electrocardiogram signal by the third constant to generate a third product signal, and adds the third product signal to the first product signal to generate a fourth chest lead signal of the 12-lead electrocardiogram-like signal, the computing circuit multiplies the second electrocardiogram signal by the third constant to generate a fourth product signal, multiplies the sum signal by the second constant to generate a fifth product signal, and adds the fifth product signal to the fourth product signal to generate a fifth chest lead signal of the 12-lead electrocardiogram-like signal, and the computing circuit multiplies the third electrocardiogram signal by the second constant to generate a sixth product signal, and adds the sixth product signal to the fourth product signal to generate a sixth chest lead signal of the 12-lead electrocardiogram-like signal.

11. The single-arm electrocardiogram signal measurement device according to claim 1, further comprising:

a fixing unit, wherein the first sensing electrode, the second sensing electrode, the third sensing electrode, the fourth sensing electrode, the fifth sensing electrode, and the sixth sensing electrode are fixed on the six positioning points on the upper arm through the fixing unit.

12. A single-arm electrocardiogram signal measurement method, comprising:

receiving a plurality of physiological signals from six different positioning points located on an upper arm of a user using a first sensing electrode, a second sensing electrode, a third sensing electrode, a fourth sensing electrode, a fifth sensing electrode, and a sixth sensing electrode;

generating a plurality of electrocardiogram signals according to the plurality of physiological signals; and generating a 12-lead electrocardiogram-like signal according to the plurality of electrocardiogram signals.

13. The single-arm electrocardiogram signal measurement method according to claim 12, wherein:

the first sensing electrode receives a first physiological signal from a positioning point located at a front end of the upper arm, the second sensing electrode receives a second physiological signal from a positioning point shifted 45±10° towards an outside of the upper arm from the front end, the third sensing electrode receives a third physiological signal from a positioning point shifted 90±10° towards the outside of the upper arm from the front end, the fourth sensing electrode receives a fourth physiological signal from a positioning point located at a rear end of the upper arm, the fifth sensing electrode receives a fifth physiological signal from a positioning point shifted 67.5=10° towards an inside of the upper arm from the front end, and the sixth sensing electrode receives a sixth physiological signal from a positioning point shifted 112.5±10° towards the inside of the upper arm from the front end.

14. The single-arm electrocardiogram signal measurement method according to claim 13, wherein generating the plurality of electrocardiogram signals according to the plurality of physiological signals comprises:

generating a first electrocardiogram signal according to a potential difference between the second physiological signal and the sixth physiological signal;

generating a second electrocardiogram signal according to a potential difference between the first physiological signal and the fourth physiological signal;

generating a third electrocardiogram signal according to a potential difference between the third physiological signal and the first physiological signal;

generating a fourth electrocardiogram signal according to a potential difference between the third physiological signal and the fifth physiological signal; and generating a fifth electrocardiogram signal according to a potential difference between the third physiological signal and the sixth physiological signal.

15. The single-arm electrocardiogram signal measurement method according to claim 14, wherein generating the 12-lead electrocardiogram-like signal according to the plurality of electrocardiogram signals comprises:

multiplying the first electrocardiogram signal by a first constant to generate a first bipolar limb lead signal of the 12-lead electrocardiogram-like signal; and multiplying the second electrocardiogram signal by the first constant to generate a second bipolar limb lead signal of the 12-lead electrocardiogram-like signal.

16. The single-arm electrocardiogram signal measurement method according to claim 15, wherein generating the 12-lead electrocardiogram-like signal according to the plurality of electrocardiogram signals further comprises:

subtracting the first electrocardiogram signal from the second electrocardiogram signal to generate a third bipolar limb lead signal of the 12-lead electrocardiogram-like signal.

17. The single-arm electrocardiogram signal measurement method according to claim 14, wherein generating the 12-lead electrocardiogram-like signal according to the plurality of electrocardiogram signals comprises:

dividing the first electrocardiogram signal by 2 to generate a first partial pressure signal, dividing the second electrocardiogram signal by 2 to generate a second partial pressure signal, and subtracting the second partial pressure signal from an inverted signal of the first partial pressure signal to generate a first augmented unipolar limb lead signal of the 12-lead electrocardiogram-like signal.

18. The single-arm electrocardiogram signal measurement method according to claim 17, wherein generating the 12-lead electrocardiogram-like signal according to the plurality of electrocardiogram signals further comprises:

subtracting the first electrocardiogram signal from the second electrocardiogram signal to generate a differential signal, dividing the differential signal by 2 to generate a third partial pressure signal, and subtracting the third partial pressure signal from the first partial pressure signal to generate a second augmented unipolar limb lead signal of the 12-lead electrocardiogram-like signal.

19. The single-arm electrocardiogram signal measurement method according to claim 18, wherein generating the 12-lead electrocardiogram-like signal according to the plurality of electrocardiogram signals further comprises:

adding the third partial pressure signal to the first partial pressure signal to generate a third augmented unipolar limb lead signal of the 12-lead electrocardiogram-like signal.

20. The single-arm electrocardiogram signal measurement method according to claim 14, wherein generating the 12-lead electrocardiogram-like signal according to the plurality of electrocardiogram signals comprises:

generating a plurality of chest lead signals of the 12-lead electrocardiogram-like signal according to the second electrocardiogram signal, the third electrocardiogram signal, the fourth electrocardiogram signal, and the fifth electrocardiogram signal.

* * * * *